(12) United States Patent
Belson (10) Patent No.: US 9,968,290 B2
(45) Date of Patent: May 15, 2018

(54) APPARATUS AND METHODS FOR CAPSULE ENDOSCOPY OF THE ESOPHAGUS

(75) Inventor: Amir Belson, Los Altos, CA (US)

(73) Assignee: GIVEN IMAGING LTD., Yoqneam (IL)

( * ) Notice: Subject to any disclaimer, the term of this patent is extended or adjusted under 35 U.S.C. 154(b) by 504 days.

(21) Appl. No.: 11/631,277

(22) PCT Filed: Jun. 30, 2005

(86) PCT No.: PCT/US2005/023835
§ 371 (c)(1),
(2), (4) Date: Feb. 18, 2010

(87) PCT Pub. No.: WO2006/005075
PCT Pub. Date: Jan. 12, 2006

(65) Prior Publication Data
US 2011/0060189 A1    Mar. 10, 2011

Related U.S. Application Data

(60) Provisional application No. 60/584,503, filed on Jun. 30, 2004, provisional application No. 60/627,783, filed on Nov. 12, 2004.

(51) Int. Cl.
*A61B 1/00* (2006.01)
*A61B 1/04* (2006.01)
(Continued)

(52) U.S. Cl.
CPC ........ *A61B 5/4233* (2013.01); *A61B 1/00158* (2013.01); *A61B 1/041* (2013.01);
(Continued)

(58) Field of Classification Search
USPC ........ 600/103, 109, 114, 117, 118, 160, 178, 600/11–14; 606/130
See application file for complete search history.

(56) References Cited

U.S. PATENT DOCUMENTS

| 2,863,458 A | 12/1958 | Mondy et al. |
| 3,043,309 A | 7/1962 | Frank |

(Continued)

FOREIGN PATENT DOCUMENTS

| IL | 143259 | 5/2001 |
| WO | WO 2004045395 | 6/2004 |

OTHER PUBLICATIONS

U.S. Appl. No. 08/503,350, filed Jul. 17, 1995.
(Continued)

*Primary Examiner* — Timothy J Neal
*Assistant Examiner* — Aaron B Fairchild
(74) *Attorney, Agent, or Firm* — Pearl Cohen Zedek Latzer Baratz LLP (57) ABSTRACT

Apparatus and methods for capsule endoscopy are described for locating, positioning, steering, aiming and tracking of an endoscopy capsule (100) within a patient's esophagus and stomach. The apparatus includes an endoscopy capsule (100) with a magnetic element (110), an external capsule positioning system (200) including at least one magnet (202) movable along a track (204) for positioning the endoscopy capsule (100) within a patient. Also described are apparatus and methods for performing endoscopic spectroscopy using different wavelengths of light and other imaging technologies to diagnose various disease conditions, such as premalignant or inflammatory changes and internal bleeding.

14 Claims, 9 Drawing Sheets

(51) Int. Cl.
 *A61B 5/00* (2006.01)
 *A61B 34/00* (2016.01)
 *A61B 8/12* (2006.01)

(52) U.S. Cl.
 CPC .......... *A61B 5/0075* (2013.01); *A61B 5/0084* (2013.01); *A61B 34/73* (2016.02); *A61B 5/0071* (2013.01); *A61B 8/12* (2013.01)

(56) References Cited

U.S. PATENT DOCUMENTS

| | | | |
|---|---|---|---|
| 3,358,676 | A | 12/1967 | Frei et al. |
| 3,986,493 | A | 10/1976 | Hendren, III |
| 4,244,362 | A | 1/1981 | Anderson |
| 5,270,675 | A * | 12/1993 | Mori et al. .................... 335/128 |
| 5,353,807 | A | 10/1994 | Demarco |
| 5,383,467 | A | 1/1995 | Auer et al. |
| 5,413,108 | A | 5/1995 | Alfano |
| 5,421,337 | A | 6/1995 | Richards-kortum et al. |
| 5,439,000 | A | 8/1995 | Gunderson et al. |
| 5,507,287 | A | 4/1996 | Palcic et al. |
| 5,590,660 | A | 1/1997 | MacAulay et al. |
| 5,601,087 | A | 2/1997 | Gunderson et al. |
| 5,604,531 | A | 2/1997 | Iddan et al. |
| 5,647,368 | A | 7/1997 | Zeng et al. |
| 5,681,260 | A | 10/1997 | Ueda et al. |
| 5,762,613 | A | 6/1998 | Sutton et al. |
| 5,769,792 | A | 6/1998 | Palcic et al. |
| 5,827,190 | A | 10/1998 | Palcic et al. |
| 6,015,414 | A | 1/2000 | Werp et al. |
| 6,066,102 | A | 5/2000 | Townsend et al. |
| 6,096,289 | A | 8/2000 | Goldenberg |
| 6,129,667 | A | 10/2000 | Dumoulin et al. |
| 6,129,683 | A | 10/2000 | Sutton et al. |
| 6,174,291 | B1 | 1/2001 | Mcmahon et al. |
| D457,236 | S | 5/2002 | Meron et al. |
| D457,621 | S | 5/2002 | Meron et al. |
| D457,948 | S | 5/2002 | Meron et al. |
| 6,428,469 | B1 | 8/2002 | Iddan et al. |
| D464,425 | S | 10/2002 | Meron et al. |
| D469,864 | S | 2/2003 | Meron et al. |
| 6,584,348 | B2 | 6/2003 | Glukhovsky |
| 6,607,301 | B1 | 8/2003 | Glukhovsky et al. |
| 6,632,171 | B2 | 10/2003 | Iddan et al. |
| 6,632,175 | B1 | 10/2003 | Marshall |
| 6,709,387 | B1 | 3/2004 | Glukhovsky et al. |
| 6,836,377 | B1 | 12/2004 | Kislev et al. |
| 6,884,213 | B2 | 4/2005 | Raz et al. |
| 6,904,308 | B2 | 6/2005 | Frisch et al. |
| 6,934,573 | B1 | 8/2005 | Glukhovsky et al. |
| 6,939,290 | B2 | 9/2005 | Iddan |
| 6,950,690 | B1 | 9/2005 | Meron et al. |
| 6,958,034 | B2 | 10/2005 | Iddan |
| 6,986,738 | B2 | 1/2006 | Glukhovsky et al. |
| 7,009,634 | B2 | 3/2006 | Iddan et al. |
| 7,083,578 | B2 | 8/2006 | Lewkowicz et al. |
| 7,161,164 | B2 | 1/2007 | Glukhovsky |
| 7,201,872 | B2 | 4/2007 | Meron et al. |
| 7,295,226 | B1 | 11/2007 | Meron et al. |
| 7,311,107 | B2 | 12/2007 | Harel et al. |
| 7,468,044 | B2 | 12/2008 | Iddan |
| 7,485,093 | B2 | 2/2009 | Glukhovsky |
| 7,505,062 | B2 | 3/2009 | Davidson et al. |
| 7,616,238 | B2 | 11/2009 | Avni |
| 7,684,840 | B2 | 3/2010 | Palti |
| 7,708,705 | B2 | 5/2010 | Iddan et al. |
| 7,727,169 | B1 | 6/2010 | Lewkowizc et al. |
| 7,866,322 | B2 | 1/2011 | Iddan |
| 7,877,134 | B2 | 1/2011 | Glukhovsky |
| 7,907,986 | B2 | 3/2011 | Lewkowicz et al. |
| 2002/0042562 | A1 | 4/2002 | Meron et al. |
| 2002/0093484 | A1 | 7/2002 | Skala et al. |
| 2002/0107444 | A1 | 8/2002 | Adler |
| 2002/0109774 | A1 | 8/2002 | Meron et al. |
| 2002/0146834 | A1 | 10/2002 | Meron et al. |
| 2002/0158976 | A1 | 10/2002 | Avni et al. |
| 2002/0165592 | A1 | 11/2002 | Glukhovsky et al. |
| 2002/0177779 | A1 | 11/2002 | Glukhovsky et al. |
| 2003/0018280 | A1 | 1/2003 | Glukhovsky et al. |
| 2003/0028078 | A1 | 2/2003 | Glukhovsky |
| 2003/0040685 | A1 | 2/2003 | Glukhovsky et al. |
| 2003/0043263 | A1 | 3/2003 | Glukhovsky et al. |
| 2003/0045790 | A1 | 3/2003 | Lewkowicz et al. |
| 2003/0077223 | A1 | 4/2003 | Glukhovsky et al. |
| 2003/0117491 | A1 | 6/2003 | Glukhovsky et al. |
| 2003/0139647 | A1 | 7/2003 | Raz et al. |
| 2003/0167007 | A1 | 9/2003 | Belson |
| 2003/0174208 | A1 | 9/2003 | Glukhovsky et al. |
| 2003/0191430 | A1 | 10/2003 | D'andrea et al. |
| 2003/0195415 | A1 | 10/2003 | Iddan |
| 2003/0229268 | A1 | 12/2003 | Uchiyama et al. |
| 2004/0050394 | A1 | 3/2004 | Jin |
| 2004/0138532 | A1 | 7/2004 | Glukhovsky |
| 2004/0138552 | A1 | 7/2004 | Harel et al. |
| 2004/0171914 | A1 | 9/2004 | Avni |
| 2004/0181127 | A1 | 9/2004 | Matsumoto et al. |
| 2005/0007555 | A1 | 1/2005 | Manabe et al. |
| 2005/0080342 | A1 | 4/2005 | Gilreath et al. |
| 2005/0215911 | A1 | 9/2005 | Alfane et al. |
| 2005/0259487 | A1 | 11/2005 | Glukhovsky et al. |
| 2006/0002017 | A1 | 1/2006 | Taguchi et al. |
| 2006/0004255 | A1 | 1/2006 | Gilad et al. |
| 2006/0004256 | A1 | 1/2006 | Gilad et al. |
| 2006/0052667 | A1 | 3/2006 | Palti et al. |
| 2008/0300458 | A1 | 12/2008 | Kim et al. |
| 2011/0060189 | A1 | 10/2011 | Belson |

OTHER PUBLICATIONS

U.S. Appl. No. 09/570,809, filed May 15, 2000 Glukhovsky et al.
"Capsule-Endoscopy in a Small Bowl Diagnostics", Racz et al. ,2003, 2;144(44):Abstract.
"Capsule Endoscopy: Can it Replace Upper Endoscopy to Screen for Barrett's Esophagus?" Schnoll-Sussman et al., 2004 Gastrointestinal cancers Symposium; Subcategory: Upper GI Cancer (Esophageal and gastric); Abstract No. 43.
"Role of Capsule Endoscopy in Patients with Portal Hypertension and Obscure Gastrointestinal Bleeding", Kovacs et al., Aug. 12, 2007;148(32):1491-7.
International Preliminary Report of Patentability for Application No. PCT/IL2008//001475 dated May 20, 2010.
Supplementary Search Report for Europe Application No. EP07790050 dated Feb. 21, 2011.

* cited by examiner

APPARATUS AND METHODS FOR CAPSULE ENDOSCOPY OF THE ESOPHAGUS

CROSS REFERENCE TO OTHER APPLICATIONS

This application is a national phase application of International Application PCT/US05/23835 filed on Jun. 30, 2005, which in turn claims priority from U.S. Provisional Application No. 60/584,503, filed on Jun. 30, 2004 and U.S. Provisional Application No. 60/627,783, filed on Nov. 12, 2004. This and all patents and patent applications referred to herein are hereby incorporated by reference in their entirety.

FIELD OF THE INVENTION

The present invention relates generally to apparatus and methods for performing capsule endoscopy. More specifically, it relates to apparatus and methods for locating, positioning, steering, aiming and tracking of an endoscopy capsule within a patient's esophagus and stomach. It also relates to apparatus and methods for performing endoscopic spectroscopy using different wavelengths of light and other imaging technologies to diagnose various disease conditions, such as premalignant or inflammatory changes, as well as internal bleeding.

BACKGROUND OF THE INVENTION

Capsule endoscopy is a method of examining the interior of a patient's gastrointestinal tract using an endoscopy capsule or "camera pill" that includes a miniaturized camera and a light source inside an ingestible capsule. Typically, the patient swallows the endoscopy capsule, which takes a series of pictures as it passes through the patient's digestive system and transmits the images to a receiver external to the patient. The endoscopy capsule passes out of the digestive system in the patient's stool and is discarded. Capsule endoscopy has proven to be most valuable in examining and diagnosing a patient's small intestine, as this portion of the gastrointestinal tract is not readily accessible using standard flexible endoscopy methods.

Recent studies have investigated the use of capsule endoscopy for examination of a patient's esophagus, particularly for diagnosing Barrett's esophagus, a precancerous condition associated with chronic gastroesophageal reflux disease (GERD). Success of these studies has been hampered in part by the fast transit time of the endoscopy capsule through the esophagus (typically 1-8 seconds), as compared to other portions of the gastrointestinal tract. The rapid transit time allows only a few images to be taken of the esophagus (typically 4-11 images) and many times the area of greatest interest at the gastroesophageal junction or "Z-line" is missed entirely. Efforts to improve the effectiveness of capsule endoscopy of the esophagus have included having the patients examined in a supine position to slow down the transit time of the capsule through the esophagus, taking more images per minute, and having patients swallow a capsule with a string attached to it to retard the passage of the capsule through the esophagus. However, these measures have not proven to be entirely effective. Even the most successful studies to date have had results that would make esophageal capsule endoscopy appropriate only as a screening tool and not as an accurate diagnostic technique.

Systems have been proposed for stereotactic positioning or steering of instruments, such as needles, catheters and endoscopy capsules, within a patient's body using externally applied magnetic fields. These systems are generally very complex and expensive, and it would be cost-prohibitive to use these systems for all routine esophageal capsule endoscopy examinations.

What is needed and has not been available heretofore is an effective and cost-efficient means for locating, positioning, steering and tracking of an endoscopy capsule within a patient's esophagus.

The following medical articles, patents and patent applications, which describe various aspects of capsule endoscopy and related technologies, are hereby incorporated by reference.

Capsule endoscopy of the esophagus?; A Németh, I Rácz; 1st Department of Internal Medicine, Petz Aladár County and Teaching Hospital, Győor; Zeitschrift für Gastroenterologie; DOI: 10.1055/s-2004-827003 lecture Capsule endoscopy: Can it replace upper endoscopy to screen for Barrett's esophagus?; F. Schnoll-Sussman, A. Hernandez, M. Bigg; 2004 Gastrointestinal Cancers Symposium; SubCategory: Upper GI Cancer (Esophageal and Gastric); Abstract No: 43

U.S. Pat. No. 6,709,387 System and method for controlling in vivo camera capture and display rate U.S. Pat. No. 6,632,171 Method for in vivo delivery of autonomous capsule U.S. Pat. No. 6,607,301 Device and method for dark current noise temperature sensing in an imaging device U.S. Pat. No. 6,584,348 Method for measurement of electrical characteristics of tissue U.S. Pat. No. D469,864 Capsule with expanded membrane U.S. Pat. No. D464,425 Tapering capsule U.S. Pat. No. 6,428,469 Energy management of a video capsule U.S. Pat. No. D457,948 Concave capsule U.S. Pat. No. D457,621 Tapering capsule U.S. Pat. No. D457,236 Capsule with a handle WO2004045395A2 SYSTEM AND METHOD FOR STRESS AND PRESSURE SENSING IN AN IN-VIVO DEVICE EP1421775A2 IN VIVO IMAGING DEVICE WITH A SMALL CROSS SECTIONAL AREA AND METHODS FOR CONSTRUCTION THEREOF

EP1418845A2 INDUCTION POWERED IN VIVO IMAGING DEVICE

EP1418844A2 A METHOD FOR IN VIVO IMAGING OF AN UNMODIFIED GASTROINTESTINAL TRACT

EP1418833A2 IN VIVO SENSING DEVICE WITH A CIRCUIT BOARD HAVING RIGID SECTIONS AND FLEXIBLE SECTIONS

WO2004039233A2 SYSTEM AND METHOD FOR IN VIVO DETECTION OF *H. PYLORI*

WO2004036803A2 DEVICE, SYSTEM AND METHOD FOR TRANSFER OF SIGNALS TO A MOVING DEVICE

WO2004035106A2 INTUBATION AND IMAGING DEVICE AND SYSTEM

EP1411818A2 APPARATUS AND METHOD FOR CONTROLLING ILLUMINATION OR IMAGER GAIN IN AN IN-VIVO IMAGING DEVICE

EP1326432A3 Device, system and method for capturing in-vivo images with three-dimensional aspects

WO2004028336A3 REDUCED SIZE IMAGING DEVICE

WO2004028336A2 REDUCED SIZE IMAGING DEVICE

WO2004028335A3 IN-VIVO SENSING SYSTEM

EP1401512A2 SYSTEM FOR CONTROLLING IN VIVO CAMERA CAPTURE AND DISPLAY RATE
EP1199975A4 AN OPTICAL SYSTEM
EP1400105A2 A METHOD FOR TIMING CONTROL
EP1399201A2 DEVICE AND SYSTEM FOR IN-VIVO PROCEDURES
EP1397660A2 A FLOATABLE IN VIVO SENSING DEVICE
EP1393567A2 SYSTEM AND METHOD FOR WIDE FIELD IMAGING OF BODY LUMENS
WO2004014227A1 SYSTEM FOR IN VIVO SAMPLING AND ANALYSIS
WO2004004540A3 SYSTEM AND METHOD FOR SENSING IN-VIVO STRESS AND PRESSURE
WO2004004540A2 SYSTEM AND METHOD FOR SENSING IN-VIVO STRESS AND PRESSURE
EP1372474A2 METHOD AND SYSTEM FOR DETECTING COLORIMETRIC ABNORMALITIES
WO2003094723A1 SYSTEM AND METHOD FOR IN VIVO SENSING
WO2003090618A3 DEVICE AND METHOD FOR ORIENTING A DEVICE IN VIVO
WO2003090618A2 DEVICE AND METHOD FOR ORIENTING A DEVICE IN VIVO
EP1358460A2 A SYSTEM AND METHOD FOR DETERMINING IN VIVO BODY LUMEN CONDITIONS
EP1350103A2 A SYSTEM FOR DETECTING SUBSTANCES
JP2003265405A2 IN-VIVO IMAGING SYSTEM, METHOD FOR OBTAINING IN-VIVO IMAGE AND SYSTEM AND METHOD FOR PRESENTING IMAGE
IL0154449A0 DEVICE, SYSTEM AND METHOD FOR ACCOUSTIC IN-VIVO MEASURING
IL0154421A0 A METHOD FOR TIMING CONTROL
IL0154420A0 INDUCTION POWERED IN VIVO IMAGING DEVICE
IL0154392A0 SELF PROPELLED DEVICE HAVING A MAGNETOHYDRODYNAMIC PROPULSION SYSTEM
IL0154391A0 SELF PROPELLED DEVICE
WO2003069913A1 SYSTEM AND METHOD FOR DISPLAYING AN IMAGE STREAM
JP2003220023A2 SYSTEM AND METHOD FOR MANEUVERING DEVICE IN VIVO
EP1326432A2 Device, system and method for capturing in-vivo images with three-dimensional aspects
IL0153510A0 DEVICE, SYSTEM AND METHOD FOR CAPTURING IN-VIVO IMAGES WITH THREE-DIMENSIONAL ASPECTS
WO2003053241A3 DEVICE, SYSTEM AND METHOD FOR IMAGE BASED SIZE ANALYSIS
WO2003053241A2 DEVICE, SYSTEM AND METHOD FOR IMAGE BASED SIZE ANALYSIS
CN1427692T Device and system for in vivo imaging
IL0151049A0 IN VIVO IMAGING METHODS AND DEVICES
IL0151048A0 METHOD AND SYSTEM FOR USE OF A POINTING DEVICE WITH MOVING IMAGES
WO2003028224A3 SYSTEM AND METHOD FOR CONTROLLING A DEVICE IN VIVO
WO2003028224A2 SYSTEM AND METHOD FOR CONTROLLING A DEVICE IN VIVO
WO2003021529A3 SYSTEM AND METHOD FOR THREE DIMENSIONAL DISPLAY OF BODY LUMENS
WO2003021529A2 SYSTEM AND METHOD FOR THREE DIMENSIONAL DISPLAY OF BODY LUMENS
WO2003011103A3 APPARATUS AND METHODS FOR IN VIVO IMAGING
WO2003011103A2 APPARATUS AND METHODS FOR IN VIVO IMAGING
IL0150880A0 SYSTEM AND METHOD FOR CHANGING TRANSMISSION FROM AN IN VIVO SENSING DEVICE
IL0150810A0 A SYSTEM FOR DETECTING SUBSTANCES
IL0150575A0 DEVICE AND METHOD FOR ATTENUATING RADIATION FROM IN VIVO ELECTRICAL DEVICES
WO2003010967A1 DIAGNOSTIC DEVICE USING DATA COMPRESSION
WO2003009739A3 APPARATUS AND METHOD FOR CONTROLLING ILLUMINATION OR IMAGER GAIN IN AN IN-VIVO IMAGING DEVICE
WO2003009739A2 APPARATUS AND METHOD FOR CONTROLLING ILLUMINATION OR IMAGER GAIN IN AN IN-VIVO IMAGING DEVICE
WO2003005877A2 DEVICE AND METHOD FOR EXAMINING A BODY LUMEN
WO2002073507C2 METHOD AND SYSTEM FOR DETECTING COLORIMETRIC ABNORMALITIES
EP1260176A3 Array system and method for locating an in vivo signal source
JP2003019111A2 ARRAY SYSTEM AND METHOD FOR DETECTING POSITION OF IN VIVO SIGNAL SOURCE
WO2003003706A3 IN VIVO IMAGING DEVICE WITH A SMALL CROSS SECTIONAL AREA
WO2003003706A2 IN VIVO IMAGING DEVICE WITH A SMALL CROSS SECTIONAL AREA AND METHODS FOR CONSTRUCTION THEREOF
WO2002102224A3 IN VIVO SENSING DEVICE WITH A CIRCUIT BOARD HAVING RIGID SECTIONS AND FLEXIBLE SECTIONS
WO2002102224A2 IN VIVO SENSING DEVICE WITH A CIRCUIT BOARD HAVING RIGID SECTIONS AND FLEXIBLE SECTIONS
WO2002102223A3 MOTILITY ANALYSIS WITHIN A GASTROINTESTINAL TRACT
WO2002102223A2 MOTILITY ANALYSIS WITHIN A GASTROINTESTINAL TRACT
EP1263318A2 A DEVICE AND SYSTEM FOR IN VIVO IMAGING
IL0150167A0 METHOD FOR IN VIVO SENSING
WO2002095351A3 A FLOATABLE IN VIVO SENSING DEVICE
WO2002095351A2 A FLOATABLE IN VIVO SENSING DEVICE
WO2002094337A3 A METHOD FOR IN VIVO IMAGING OF AN UNMODIFIED GASTROINTESTINAL TRACT
WO2002094337A2 A METHOD FOR IN VIVO IMAGING OF AN UNMODIFIED GASTROINTESTINAL TRACT
AU0754898B2 SYSTEM AND METHOD FOR IN VIVO DELIVERY OF AUTONOMOUS CAPSULE
EP1260176A2 Array system and method for locating an in vivo signal source
WO2002080753A3 INDUCTION POWERED IN VIVO IMAGING DEVICE
WO2002080753A2 INDUCTION POWERED IN VIVO IMAGING DEVICE
WO2002080376A3 A METHOD FOR TIMING CONTROL
WO2002080376A2 A METHOD FOR TIMING CONTROL WO2002073507A3 METHOD AND SYSTEM FOR DETECTING COLORIMETRIC ABNORMALITIES
WO2002073507A2 METHOD AND SYSTEM FOR DETECTING COLORIMETRIC ABNORMALITIES
AU0751740B2 ENERGY MANAGEMENT OF A VIDEO CAPSULE
IL0147789A0 DEVICE AND METHOD FOR POSITIONING AN OBJECT IN A BODY LUMEN
IL0147221A0 IMAGE BASED SIZE ANALYSIS
IL0147126A0 A DEVICE AND METHOD FOR TESTING A BODY LUMEN CONFIGURATION
WO2002055984A3 A SYSTEM AND METHOD FOR DETERMINING IN VIVO BODY LUMEN CONDITIONS
WO2002055984A2 A SYSTEM AND METHOD FOR DETERMINING IN VIVO BODY LUMEN CONDITIONS
WO2002055126A3 DEVICE AND SYSTEM FOR IN-VIVO PROCEDURES
WO2002055126A2 DEVICE AND SYSTEM FOR IN-VIVO PROCEDURES
WO2002054932A3 SYSTEM AND METHOD FOR WIDE FIELD IMAGING OF BODY LUMENS
WO2002054932A2 SYSTEM AND METHOD FOR WIDE FIELD IMAGING OF BODY LUMENS
AU0222460A5 METHOD AND SYSTEM FOR USE OF A POINTING DEVICE WITH MOVING IMAGES
WO200245567A3 METHOD AND SYSTEM FOR USE OF A POINTING DEVICE WITH MOVING IMAGES
WO200245567A2 METHOD AND SYSTEM FOR USE OF A POINTING DEVICE WITH MOVING IMAGES
IL0144296A0 A DEVICE AND METHOD FOR TESTING A BODY LUMEN CONFIGURATION
EP1199975A1 AN OPTICAL SYSTEM
IL0143418A0 MEASUREMENT OF ELECTRICAL CHARACTERISTICS OF TISSUE
IL0143260A0 ARRAY SYSTEM AND METHOD FOR LOCATING AN IN VIVO SIGNAL SOURCE
IL0143259A0 A METHOD FOR MOVING AN OBJECT THROUGH THE COLON
IL0143258A0 A METHOD FOR IN VIVO IMAGING OF THE GASTROINTESTINAL TRACT IN UNMODIFIED CONDITIONS
IL0143117A0 SYSTEM FOR CONTROLLING IN VIVO CAMERA FRAME CAPTURE AND FRAME DISPLAY RATES
IL0143116A0 POWER REGIMEN FOR AN IN VIVO CAMERA SYSTEM
AU0195854A5 AN IMMOBILIZABLE IN VIVO SENSING DEVICE
WO200226103A3 AN IMMOBILIZABLE IN VIVO SENSING DEVICE
WO200226103A2 AN IMMOBILIZABLE IN VIVO SENSING DEVICE
IL0142026A0 DEVICE AND METHOD FOR IN VITRO DETECTION OF BLOOD
IL0141907A0 A DEVICE AND SYSTEM FOR IN VIVO IMAGING
JP2002010990A2 MEASUREMENT OF ELECTRIC CHARACTERISTICS OF TISSUE
EP1041919A4 SYSTEM AND METHOD FOR IN VIVO DELIVERY OF AUTONOMOUS CAPSULE
EP1117323A4 A METHOD FOR TEMPERATURE SENSING
EP1159917A1 Apparatus for measuring electrical characteristics of tissue
AU0160578A5 DEVICE AND METHOD FOR POSITIONING AN OBJECT IN A BODY LUMEN
WO200189596A3 DEVICE FOR POSITIONING OBJECT IN A BODY LUMEN
WO200189596A2 DEVICE AND METHOD FOR POSITIONING AN OBJECT IN A BODY LUMEN
AU0156640A5 SYSTEM FOR CONTROLLING IN VIVO CAMERA CAPTURE AND DISPLAY RATE
WO200187377A3 SYSTEM FOR CONTROLLING IN VIVO CAMERA CAPTURE AND DISPLAY RATE
WO200187377A2 SYSTEM FOR CONTROLLING IN VIVO CAMERA CAPTURE AND DISPLAY RATE
WO200169212A1 DEVICE AND METHOD FOR IN VITRO DETECTION OF BLOOD
EP1039830A4 ENERGY MANAGEMENT OF A VIDEO CAPSULE
AU0141004A5 A DEVICE AND SYSTEM FOR IN VIVO IMAGING
WO200165995A3 A DEVICE AND SYSTEM FOR IN VIVO IMAGING
WO200165995A2 A DEVICE AND SYSTEM FOR IN VIVO IMAGING
EP1123035A1 A METHOD FOR DELIVERING A DEVICE TO A TARGET LOCATION
WO200153792A3 A SYSTEM FOR DETECTING SUBSTANCES
WO200153792A2 A SYSTEM FOR DETECTING SUBSTANCES
EP1117323A1 A METHOD FOR TEMPERATURE SENSING
AU0114097A5 METHOD FOR ACTIVATING AN IMAGE COLLECTING PROCESS
WO200135813A1 METHOD FOR ACTIVATING AN IMAGE COLLECTING PROCESS
IL0132944A0 METHOD FOR ACTIVATING AN IMAGE COLLECTING PROCESS
AU0064656A5 A METHOD FOR TEMPERATURE SENSING
WO200110291A1 A METHOD FOR TEMPERATURE SENSING
IL0131242A0 A METHOD FOR TEMPERATURE SENSING
AU0052441A5 AN OPTICAL SYSTEM
WO200076391A1 AN OPTICAL SYSTEM
IL0110475A1 OPTICAL SYSTEM FOR FLEXIBLE TUBES
EP1041919A2 SYSTEM AND METHOD FOR IN VIVO DELIVERY OF AUTONOMOUS CAPSULE
EP1039830A1 ENERGY MANAGEMENT OF A VIDEO CAPSULE
IL0130486A0 AN OPTICAL SYSTEM
AU6364599A1 A METHOD FOR DELIVERING A DEVICE TO A TARGET LOCATION
WO200022975A1 A METHOD FOR DELIVERING A DEVICE TO A TARGET LOCATION
CA2347274AA A METHOD FOR DELIVERING A DEVICE TO A TARGET LOCATION
IL0108352A1 IN VIVO VIDEO CAMERA SYSTEM
WO199932028A3 SYSTEM AND METHOD FOR IN VIVO DELIVERY OF AUTONOMOUS CAPSULE
IL0126727A0 A METHOD FOR DELIVERING A DEVICE TO A TARGET LOCATION
AU1575899A1 SYSTEM AND METHOD FOR IN VIVO DELIVERY OF AUTONOMOUS CAPSULE
AU1574599A1 ENERGY MANAGEMENT OF A VIDEO CAPSULE
WO199932028A2 SYSTEM AND METHOD FOR IN VIVO DELIVERY OF AUTONOMOUS CAPSULE

CA2315727AA SYSTEM AND METHOD FOR IN VIVO DELIVERY OF AUTONOMOUS CAPSULE

WO199930610A1 ENERGY MANAGEMENT OF A VIDEO CAPSULE

CA2314104AA ENERGY MANAGEMENT OF A VIDEO CAPSULE

US20030191430A1 Method of using, and determining location of, an ingestible capsule U.S. Pat. No. 2,863,458 Vein Stripper and Method of Stripping Veins U.S. Pat. No. 3,043,309 Method of Performing Intestinal Intubation U.S. Pat. No. 3,358,676 Magnetic Propulsion of Diagnostic or Therapeutic Elements Through the Body Ducts of Animals or Human Patients U.S. Pat. No. 3,986,493 Electromagnetic Bougienage Method U.S. Pat. No. 4,244,362 Endotracheal Tube Control Device U.S. Pat. No. 4,278,077 Medical Camera System U.S. Pat. No. 5,353,807 Magnetically Guidable Intubation Device U.S. Pat. No. 5,681,260 Guiding Apparatus for Guiding an Insertable Body within an Inspected Object U.S. Pat. No. 6,015,414 Method and Apparatus for Magnetically Controlling Motion Direction of a Mechanically Pushed Catheter U.S. Pat. No. 6,632,175 Swallowable Data Recorder Capsule Medical Device Capsule endoscopy is also used for imaging of the small intestine, especially to look for bleeding and inflammatory bowel disease. Currently available imaging capsules, as described in the publications listed above, use only the visible spectrum of light and the images are seen as regular images.

Endoscopic spectroscopy is an emerging technology for diagnosis of cancer and other diseases within a patient's body. Spectroscopic examination can be used to identify lesions that are not readily visible using white light endoscopy and/or to diagnose or differentiate tissues of suspected lesions that are found using white light endoscopy or other techniques. Auto fluorescence is a spectroscopic technique that illuminates a patient's tissues with one or more excitation frequencies and measures and/or images the natural fluorescence of the tissues. Differences in the natural fluorescence can be used to distinguish between normal cells and certain types of diseased cells. Dye-enhanced fluorescence is a spectroscopic technique in which one or more special fluorescent marker dyes are applied to the tissues either topically or systemically. The tissues are then illuminated with one or more excitation frequencies and the fluorescence of the tissues is measured and/or imaged. Differences in the uptake of the fluorescent marker dyes can be used to identify lesions and/or to distinguish between normal cells and certain types of diseased cells. Other known spectroscopic techniques can also be used. The following U.S. patents and patent applications, each of which is incorporated herein by reference in its entirety, describe various spectroscopic techniques that can also be used in connection with the present invention:

US20030167007 Apparatus and method for spectroscopic examination of the colon

U.S. Pat. No. 5,421,337 Spectral diagnosis of diseased tissue

U.S. Pat. No. 6,129,667 Luminal diagnostics employing spectral analysis

U.S. Pat. No. 6,096,289 Intraoperative intravascular and endoscopic tumor and lesion detection biopsy and therapy U.S. Pat. No. 6,174,291 Optical biopsy system and methods for tissue diagnosis U.S. Pat. No. 6,129,683 Optical biopsy forceps U.S. Pat. No. 6,066,102 Optical biopsy forceps system and method of diagnosing tissue U.S. Pat. No. 5,762,613 Optical biopsy forceps U.S. Pat. No. 5,601,087 System for diagnosing tissue with guidewire U.S. Pat. No. 5,439,000 Method of diagnosing tissue with guidewire U.S. Pat. No. 5,383,467 Guidewire catheter and apparatus for diagnostic imaging U.S. Pat. No. 5,413,108 Method and apparatus for mapping a tissue sample for and distinguishing different regions thereof based on luminescence measurements of cancer-indicative native fluorophor U.S. Pat. No. 5,827,190 Endoscope having an integrated CCD sensor U.S. Pat. No. 5,769,792 Endoscopic imaging system for diseased tissue U.S. Pat. No. 5,647,368 Imaging system for detecting diseased tissue using native fluorescence in the gastrointestinal and respiratory tract U.S. Pat. No. 5,590,660 Apparatus and method for imaging diseased tissue using integrated auto fluorescence U.S. Pat. No. 5,507,287 Endoscopic imaging system for diseased tissue

DESCRIPTION OF THE INVENTION

Figure 1A:
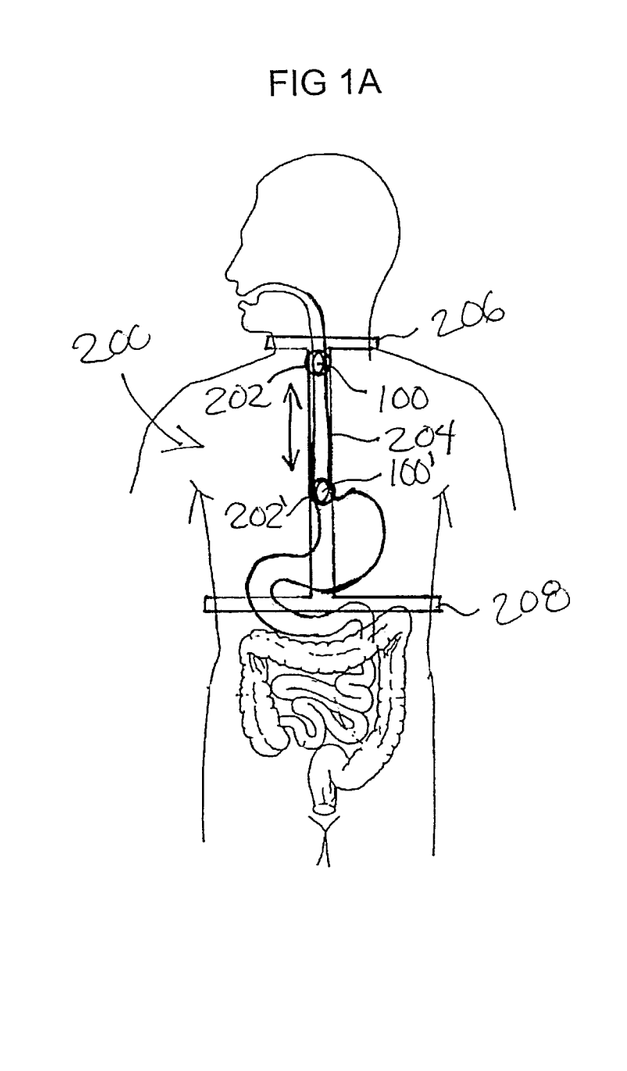
FIGS. 1A and 1B show a first embodiment of the apparatus of the invention, which includes an ingestible endoscopy capsule and an external capsule positioning system, in use for performing esophageal capsule endoscopy on a patient.
Figure 1B:
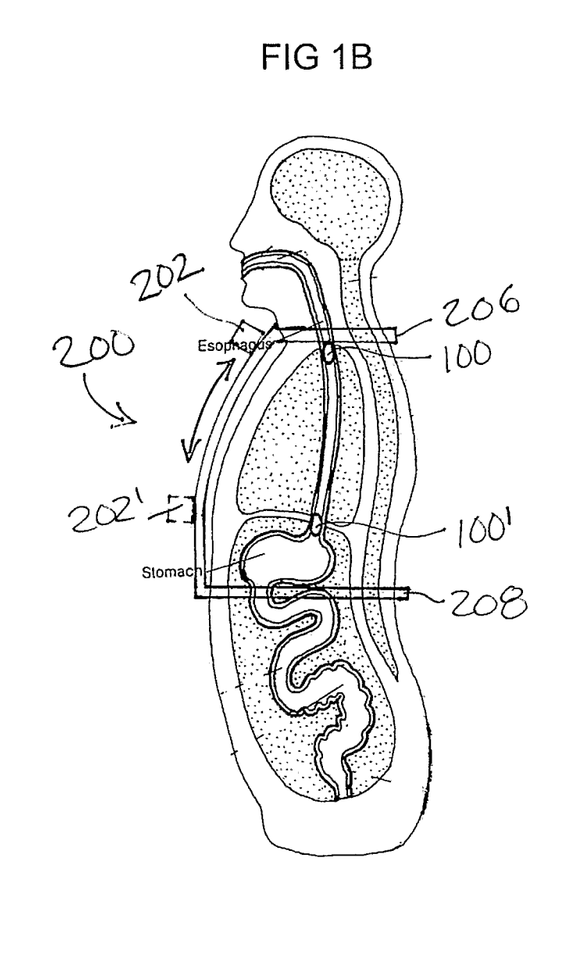

FIGS. 1A and 1B show a first embodiment of the apparatus of the invention in use for performing esophageal capsule endoscopy on a patient. The apparatus includes an ingestible endoscopy capsule 100 and an external capsule positioning system 200. The endoscopy capsule 100, which will be described in greater detail below, includes a magnetically attracted element, which may be a permanent magnet, an electromagnet or a magnetically attracted ferritic material. The external capsule positioning system 200 includes at least one external magnet 202, which may be a permanent magnet or an electromagnet, and means for positioning the external magnet 202 with respect to the patient's anatomy.

In one particularly preferred embodiment, the means for positioning the external magnet 202 includes a track 204, which is configured to be positioned over the esophagus on the ventral or anterior surface of the patient's torso. The track 204 is approximately linear when viewed from the anterior of the patient, as shown in FIG. 1A. Alternatively, the track 204 may be made in a curved configuration to accommodate patients whose esophagus cannot be approximated with a linear track. Viewed from the side, as in FIG. 1B, the track 204 may be straight or curved and it may be rigid or flexible to conform to the curvature of the patient's torso. The track 204 is preferably long enough to extend at least from the patient's epiglottis to the stomach. The external magnet 202 can be moved up and down the track 204 manually or the movement of the external magnet 202 may be motorized. An alternative configuration of the positioning system 200 could use a continuous loop cable or drive belt or other linear actuator in place of the linear track 204 for moving the external magnet 202 up and down the patient's torso over the esophagus.

Preferably, the positioning system 200 includes means for fastening the track 204 to the patient's torso in a desired position over the esophagus. For example, the positioning system 200 may include a collar 206 and a waist belt 208 for fastening the track 204 to the patient, as shown in FIGS. 1A and 1B. Alternatively, the track 204 could be attached to a garment that is then fastened to the patient. The garment could be in the shape of a vest, apron or poncho. Alternatively, the track 204 could be attached to the patient in the correct position using adhesive tape or the like.

The positioning system 200 may include a position sensor for sensing the position of the external magnet 202 along the track 204, which will correlate with the position of the endoscopy capsule 100 within the esophagus. The position information can be collected and correlated with the images taken by the endoscopy capsule 100 so that the location of any suspicious lesions can be accurately pinpointed for further diagnostic tests, biopsy or treatment. In addition, the position information can be used by a computer to construct an accurate three-dimensional image or mathematical model of the esophagus from the images collected.

In use, the external capsule positioning system 200 is fastened to the patient, with the track 204 positioned over the esophagus. The external magnet 202 is positioned near the top of the patient's esophagus. If the external magnet 202 is an electromagnet, it should be energized at this time.

The patient is then asked to swallow the endoscopy capsule 100, which moves into the esophagus, but stays at the top of the esophagus and does not descend because it is attracted to the external magnet 202. The system may include a sensor to detect when the endoscopy capsule 100 is captured and held by the external magnet 202. Optionally, a light or other indicator will show when the endoscopy capsule 100 is captured and held by the external magnet 202. The external magnet 202 is moved downward slowly so that the endoscopy capsule 100 can capture a sufficient number of images, either still images and/or video images, to make a reliable diagnosis. If the physician wants to examine any particular area more closely, the movement of the endoscopy capsule 100 can be stopped or even reversed. The external magnet 202 can be moved up and down the track 204 manually or the movement of the external magnet 202 may be motorized.

The images can be transmitted by the endoscopy capsule 100 to an external receiver (not shown) and/or they can be stored in an electronic memory within the endoscopy capsule 100.

Generally, the examination continues until the endoscopy capsule 100' reaches the gastroesophageal junction or "Z-line", which is of particular interest in diagnosing Barrett's esophagus. Multiple images can be made of this area by slowing or stopping the descent of the endoscopy capsule 100'. In cases where the physician wishes to have a controlled examination of the stomach, the procedure can be continued into the stomach using the endoscopy capsule 100 and the external magnet 202 for guidance.

Once the esophageal examination is complete, the endoscopy capsule 100' can be released so that it will travel through the rest of the patient's digestive system. This is done by lifting the external magnet 202' or turning it off if an electromagnet is used. If desired, the endoscopy capsule 100' can be used to examine the rest of the patient's digestive system as it passes through.

Figure 13:
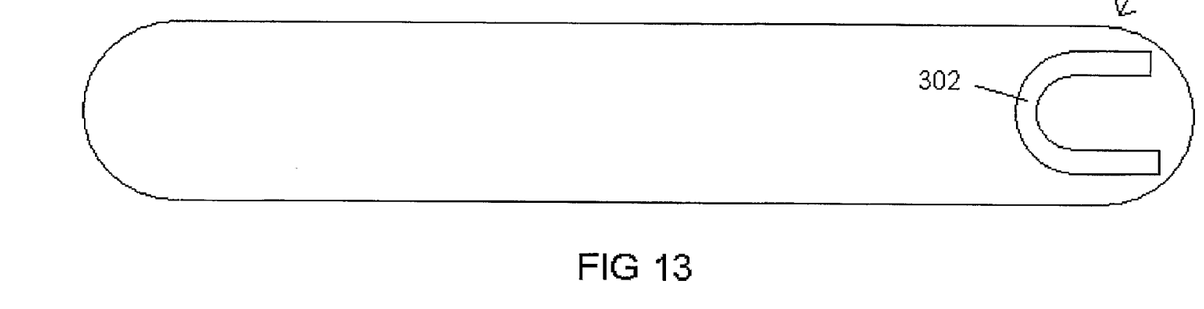
FIG. 13 shows a magnetic probe in the shape of a tongue depressor for retrieving the esophageal capsule after use.

Alternatively, the endoscopy capsule 100 can be retrieved by moving the external magnet 202 to the top of the track 204. Then a magnetic probe 300, which may be in the shape of a tongue depressor as shown in FIG. 13, is inserted through the patient's mouth. The endoscopy capsule 100 is released by lifting the external magnet 202, or turning it off if an electromagnet is used, so that the magnetic probe 300 can capture and retrieve the endoscopy capsule 100. The magnet 302 in the magnetic probe 300 can be a permanent magnet or an electromagnet.

Retrieving the endoscopy capsule 100 in this manner is especially useful when the capsule is used for taking biopsy samples or the like because it is quicker, more convenient and more certain than collecting the capsule from the patient's stool. Laboratory results will not be delayed by the transit time of the capsule through the intestines. It also eliminates the possibility that a biopsy device in the capsule would contaminate the rest of the digestive tract with malignant cells or other hazardous material.

An optional accessory to the endoscopic imaging system, which could be used in combination with or separately from the external positioning system 200, is a device in the form of a collar or necklace with a permanent magnet or electromagnet for holding the imaging capsule 100 at the top of the esophagus. The collar device may be configured similar to the collar 206 component of the external positioning system 200 described above without the track 204 attached. When it is time to release the imaging capsule 100 to begin imaging the esophagus, the external magnet can be lifted away from the patient, or de-energized in the case of an electromagnet. The collar device can also be used to capture and hold the imaging capsule 100 at the end of the procedure until it can be retrieved, for example using the magnetic probe 300 shown in FIG. 13. The collar device may include a sensor to detect when the endoscopy capsule 100 is captured and held by the external magnet. Optionally, a light or other indicator will show when the endoscopy capsule 100 is captured and held by the external magnet.

Figure 2A:
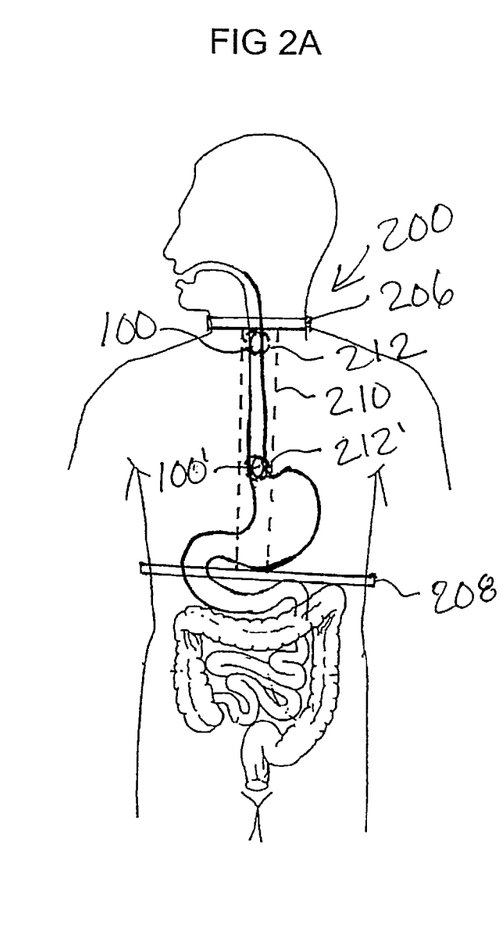
FIGS. 2A and 2B show a second embodiment of the apparatus of the invention in use for performing esophageal capsule endoscopy on a patient.
Figure 2B:
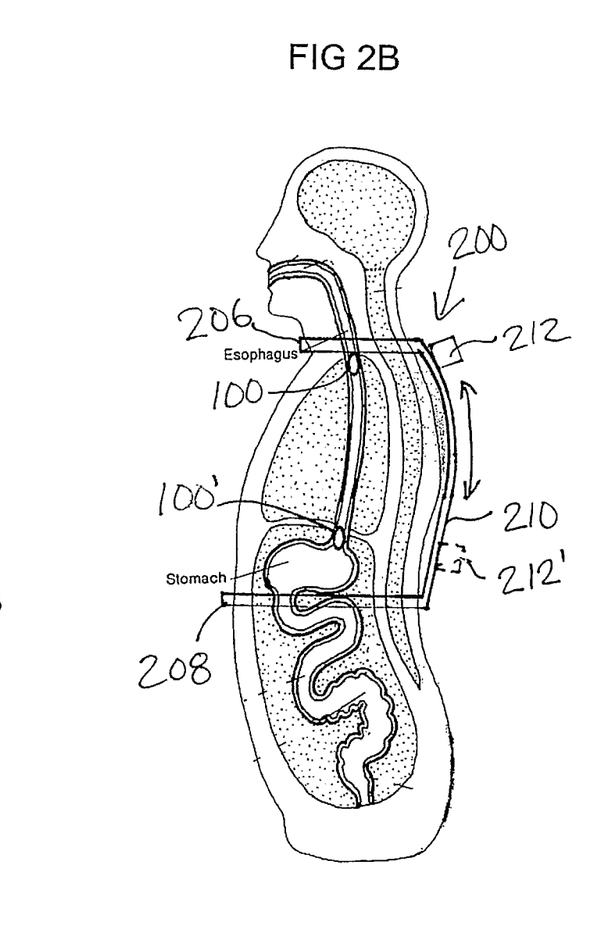

FIGS. 2A and 2B show a second embodiment of the apparatus of the invention where the external capsule positioning system 200 is fastened to the patient with a track 210 carrying an external magnet 212 positioned over the esophagus on the patient's dorsal or posterior side.

Figure 3A:
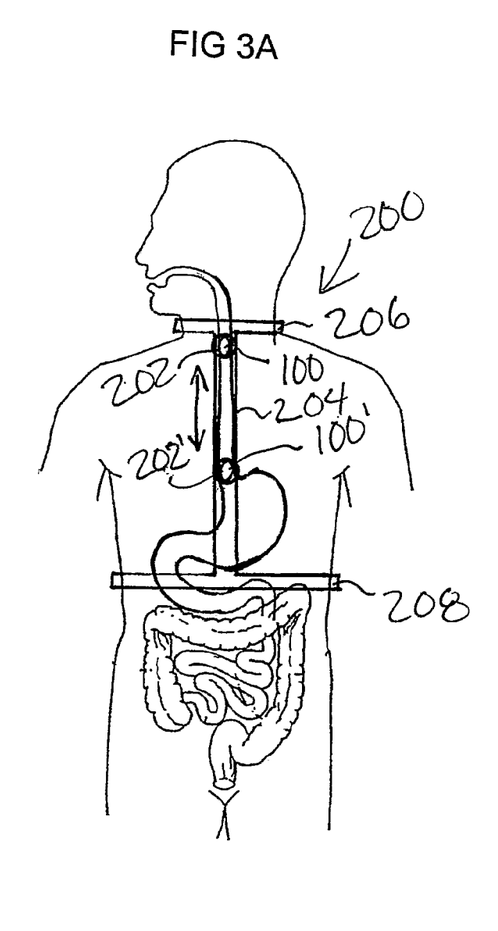
FIGS. 3A and 3B show a third embodiment of the apparatus of the invention in use for performing esophageal capsule endoscopy on a patient.
Figure 3B:
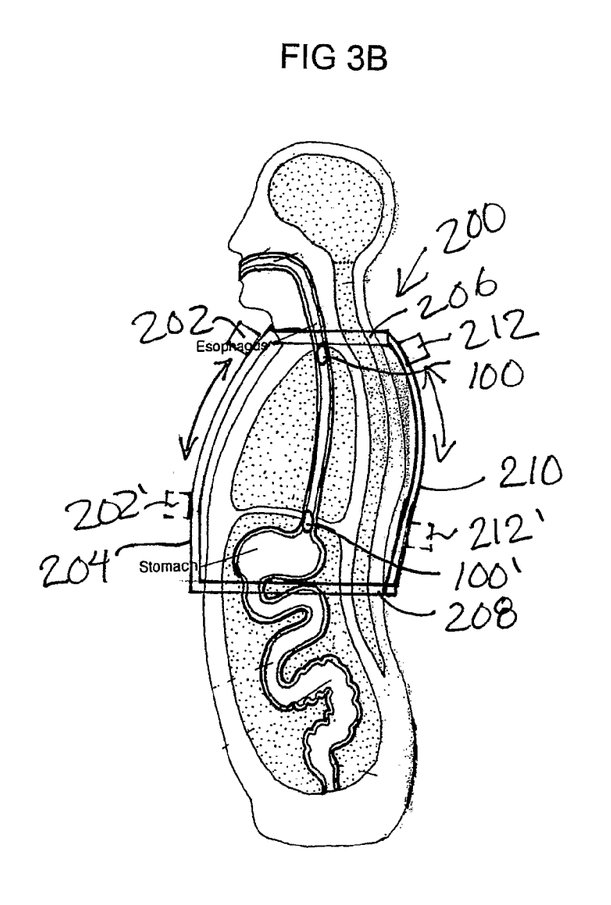

FIGS. 3A and 3B show a third embodiment of the apparatus of the invention where the external capsule positioning system 200 includes an anterior track 204 carrying a first external magnet 202 and a posterior track 210 carrying a second external magnet 212. The anterior track 204 and posterior track 210 are positioned approximately parallel to one another by the collar 206 and the waist belt 208. The first external magnet 202 and the second external magnet 212 are preferably positioned with opposite poles of the magnets facing toward the patient. The use of two external magnets in this configuration helps to center the endoscopy capsule 100 within the esophagus and minimizes the bias of the endoscopy capsule 100 to follow the anterior or posterior wall of the esophagus. In addition to moving the endoscopy capsule 100 up and down the esophagus, the two external magnets can also be used to selectively aim the camera of the endoscopy capsule 100, as will be explained further below.

Figure 4:
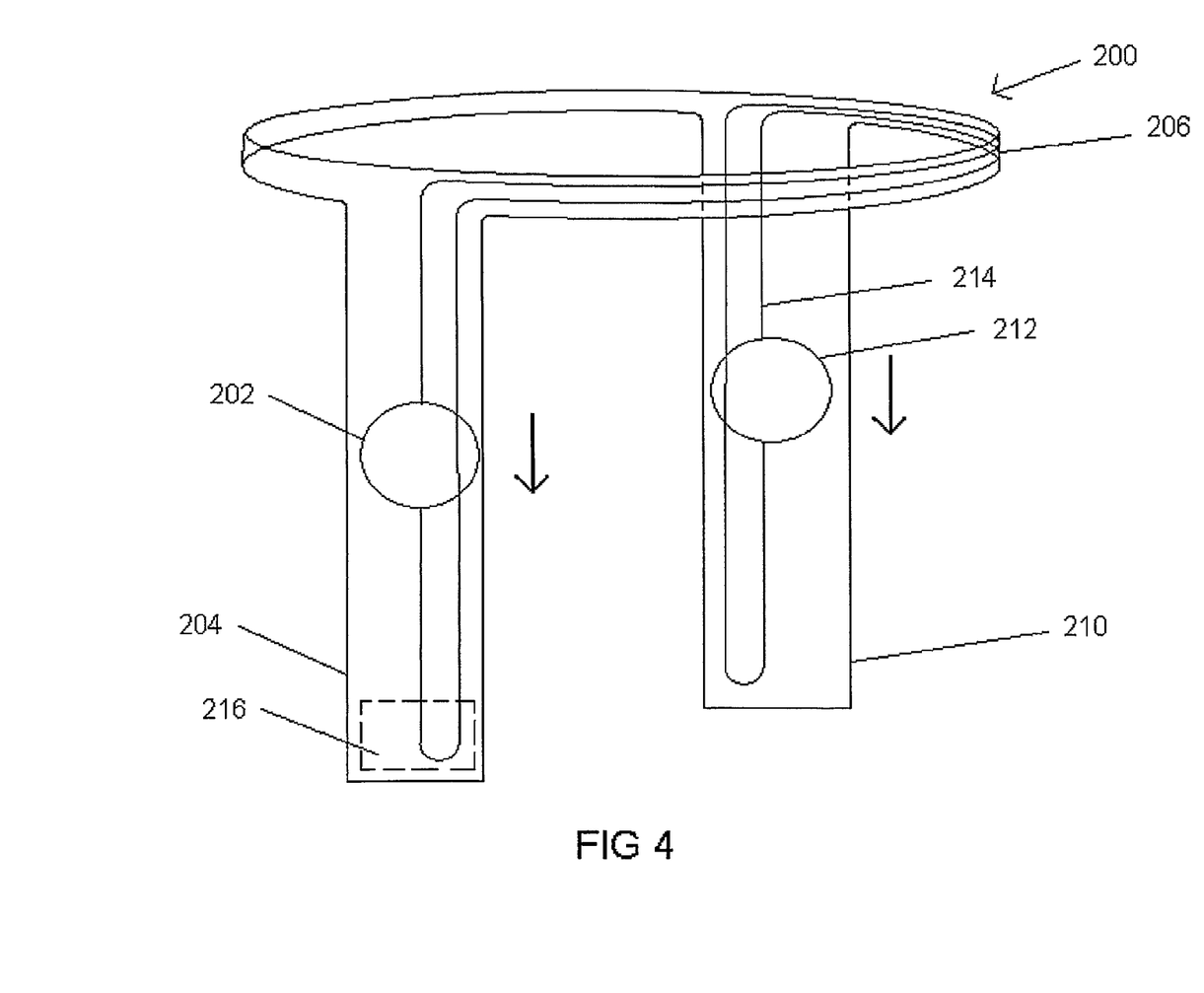
FIG. 4 is a schematic diagram of a synchronous drive mechanism for use in the apparatus of FIGS. 3A and 3B.

Preferably, the external capsule positioning system 200 is configured so that the first external magnet 202 and the second external magnet 212 will move synchronously up and down the torso of the patient. FIG. 4 is a schematic diagram of a synchronous drive mechanism for use in the apparatus of FIGS. 3A and 3B. The first external magnet 202 and the second external magnet 212 are attached to a continuous cord or cable 214 that runs in a groove and/or over pulleys in the anterior track 204 and posterior track 210 and through a connecting member, such as the collar 206 or waist belt (not shown). The synchronous drive mechanism is configured so that, when the first external magnet 202 moves up or down, the second external magnet 212 moves up or down synchronously with it. The movement of the first external magnet 202 and the second external magnet 212 may be controlled manually, or the external capsule positioning system 200 may include an electric motor 216 configured to drive the cable 214. Other mechanisms, such as synchronized linear actuators, may be used to achieve synchronous movement of the first external magnet 202 and the second external magnet 212.

The electric motor 216 may include a rotary encoder for sensing the position of the first and second external magnets 202, 212 along the tracks 204, 210, which will correlate with the position of the endoscopy capsule 100 within the esophagus.

In FIGS. 1A-3B, the external magnets 202, 212 are shown riding on the outside of the anterior and posterior tracks 204, 210, which is particularly convenient for manual movement of the magnets. Alternatively, the external magnets 202, 212 may be disc-shaped or another low profile configuration so that they can be recessed into or enclosed within the anterior and posterior tracks 204, 210 without sticking out beyond the outer surface of the tracks. This configuration would be particularly adaptable for use with an electrically driven embodiment of the external capsule positioning system 200.

Figures 5, 6, 7:
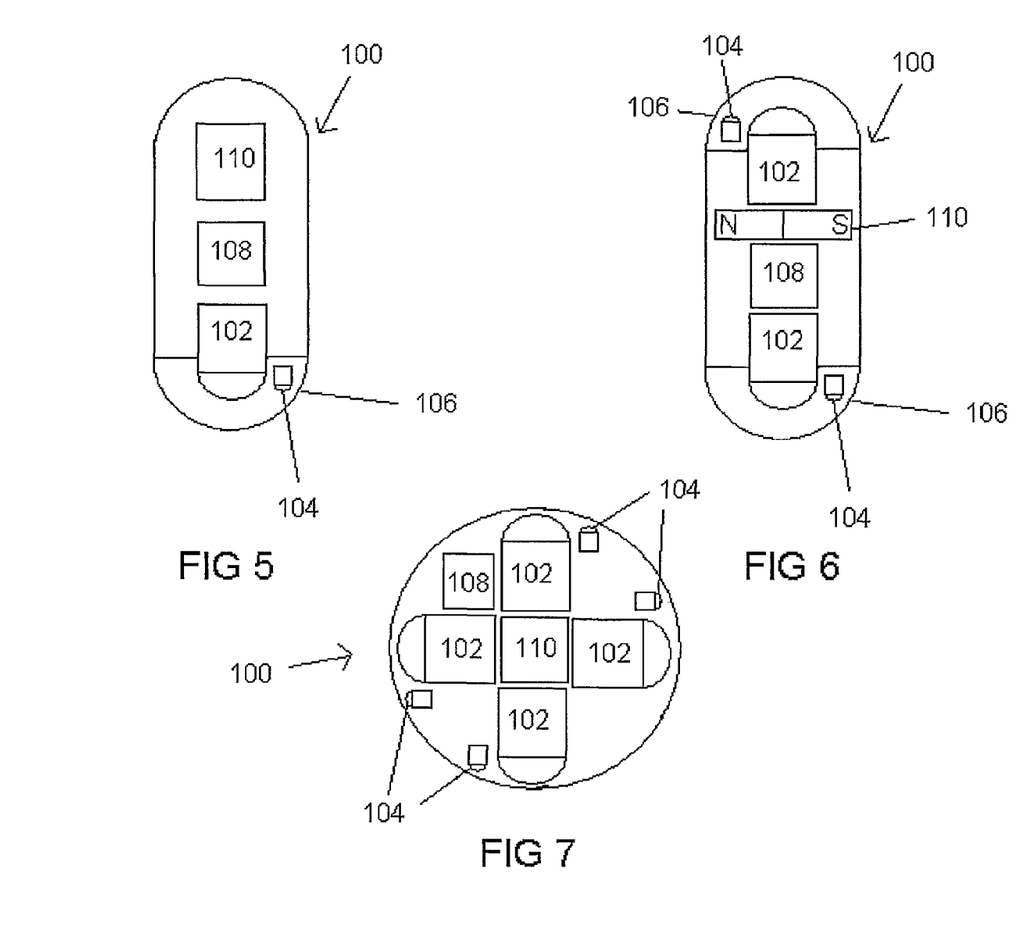
FIG. 5 shows an endoscopy capsule for use in the invention.
FIG. 6 shows an endoscopy capsule configured with two cameras.
FIG. 7 shows a spherical endoscopy capsule with a spherical imaging system.

FIG. 5 shows an endoscopy capsule 100 for use in the present invention. In this embodiment, the endoscopy capsule 100 has an external shape that is approximately ellipsoidal. The elongated ellipsoidal shape of the endoscopy capsule 100 tends to keep it in an approximately vertical orientation within the esophagus. In alternate embodiments, the endoscopy capsule 100 may have an external shape that is spherical or oblong, for example in the shape of an American football or rugby football. A miniature imaging camera 102 for still and/or video images, such as a CCD camera, and a light source 104 are positioned at one end of the endoscopy capsule 100 looking outward through a lens 106. The light source 104 can be incandescent, fluorescent, chemoluminescent, a light emitting diode (LED) or a laser diode. The endoscopy capsule 100 also includes control circuitry, image transmitting and/or image storage circuitry and a power source, such as a battery, shown generally by reference number 108. The endoscopy capsule 100 includes a magnetically attracted element 110, which may be a permanent magnet, an electromagnet or a magnetically attracted ferritic material. By way of example, the endoscopy capsule 100 of FIG. 5 is shown with a magnetically attracted element 110 of ferritic material located at the upper end of the endoscopy capsule 100. The endoscopy capsule 100 is preferably swallowed with the imaging camera 102 aimed down the esophagus for effective imaging of the gastroesophageal junction.

FIG. 6 shows an endoscopy capsule 100 similar to the one in FIG. 5, except that it is configured with one imaging camera 102 facing upward and another imaging camera 102 facing downward. Images taken from two directions may be helpful in identifying and diagnosing certain types of lesions. By way of example, the endoscopy capsule 100 of FIG. 6 is shown with a magnetically attracted element 110 made with a single bar magnet. This configuration of the magnetically attracted element 110 is useful for aiming the endoscopy capsule 100 within the esophagus, as will be explained in greater detail below.

FIG. 7 shows a spherical endoscopy capsule 100 with a spherical imaging system. The spherical endoscopy capsule 100 of FIG. 7 is shown with a magnetically attracted element 110 of ferritic material located near the center of the sphere. Because of its spherical shape, the endoscopy capsule 100 will not have a preferred orientation within the esophagus. To compensate for this, the imaging system is configured to capture images completely surrounding the capsule. This can be accomplished using multiple cameras 102 and/or one or more cameras that have a fish eye or spherical view lens or similar optical system. The spherical images created by the imaging system can be stored and converted to more conventional image projections that are more easily interpreted by the user. The processed images can be panned left, right, up and down at any point in the esophagus because a full spherical image is stored for each exposure. Although the spherical endoscopy capsule 100 may rotate while descending through the esophagus, the orientation of the images can be determined relative to the proximal and distal esophagus, which will be apparent in the images and can be tracked using image recognition software.

Figures 8A, 8B, 9:
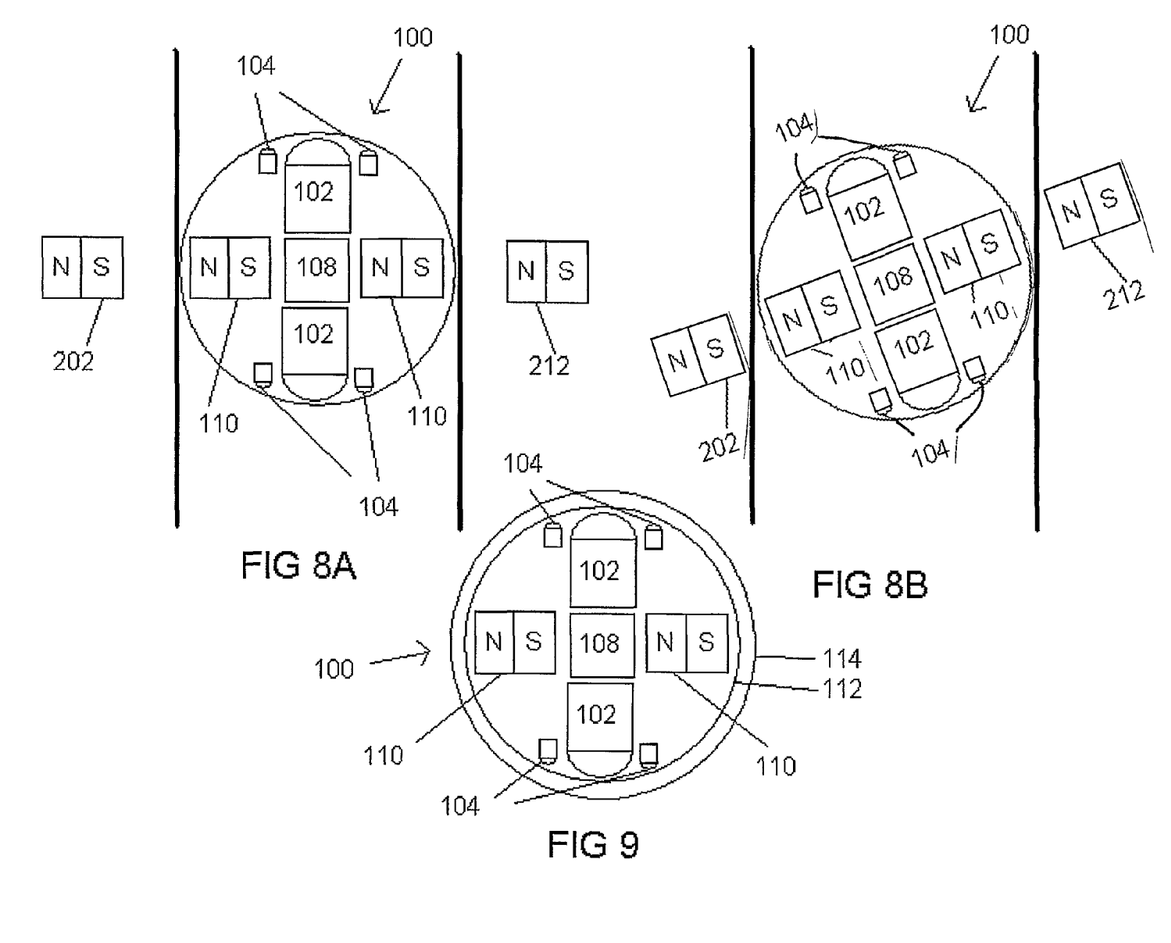
FIGS. 8A and 8B show a spherical endoscopy capsule with two cameras.
FIG. 9 shows a spherical endoscopy capsule with a rotatable inner capsule.

FIGS. 8A and 8B show a spherical endoscopy capsule 100 that may be configured with one or more imaging cameras 102. Because of its spherical shape, the endoscopy capsule 100 will not have a preferred orientation within the esophagus. To orient the imaging cameras 102 in the desired direction, the spherical endoscopy capsule 100 has a magnetically attracted element 110 configured to have a dipole moment. This can be accomplished with the use of one or more permanent magnets or electromagnets. By way of example, the endoscopy capsule 100 of FIGS. 8A and 8B is shown with a magnetically attracted element 110 made with two permanent magnets arranged to provide a dipole moment about the center of the sphere. Alternatively, the magnetically attracted element 110 may be configured with a single bar magnet that passes through the center of the sphere. This configuration of the endoscopy capsule 100 is best used with the embodiment of the external capsule positioning system 200 shown in FIGS. 3A and 3B. In FIG. 8A, the first external magnet 202 and the second external magnet 212 orient the spherical endoscopy capsule 100 so that the two imaging cameras 102 are aimed proximally and distally within the esophagus. In FIG. 8B, the first external magnet 202 and the second external magnet 212 have been rotated with respect to the patient's body to orient the spherical endoscopy capsule 100 with the two imaging cameras 102 aimed in a different desired direction. This feature can be used for close inspection of suspected lesions found in the esophagus.

In alternate embodiments, the endoscopy capsule 100 of FIGS. 8A and 8B may have an external shape that is an ellipsoid or other oblong shape, for example the shape of an American football or rugby football. In this case, the elongated shape of the endoscopy capsule 100 will tend to keep it in an approximately vertical orientation within the esophagus, except when the first and second external magnets 202, 212 are used to aim the endoscopy capsule 100 in a different orientation.

FIG. 9 shows an endoscopy capsule 100 configured with a rotatable inner capsule 112, having one or more imaging cameras 102, inside of a transparent outer capsule 114. The inner capsule 112 is rotatably suspended inside of the outer capsule 114, for example by filling the space between the inner and outer capsules 112, 114 with a liquid that provides neutral buoyancy or by mounting the inner capsule 112 on a gimbal mechanism or the like. The inner capsule 112 is preferably configured similar to the endoscopy capsule 100 of FIGS. 8A and 8B so that it can be aimed in a desired direction within the esophagus, as described above. By way of example, the magnetically attracted element 110 is configured of two permanent magnets arranged to provide a dipole moment about the center of the sphere. The inner capsule 112 is preferably spherical when fluid suspension is used, but can be almost any shaped when a gimbal mechanism is used. The transparent outer capsule 114 can be spherical as shown or it can be configured as an ellipsoid or other convenient shape. The advantage of this embodiments of the endoscopy capsule 100 is that the inner capsule 112 can be rotated to aim the imaging cameras 102 without friction against the walls of the esophagus.

Figure 10:
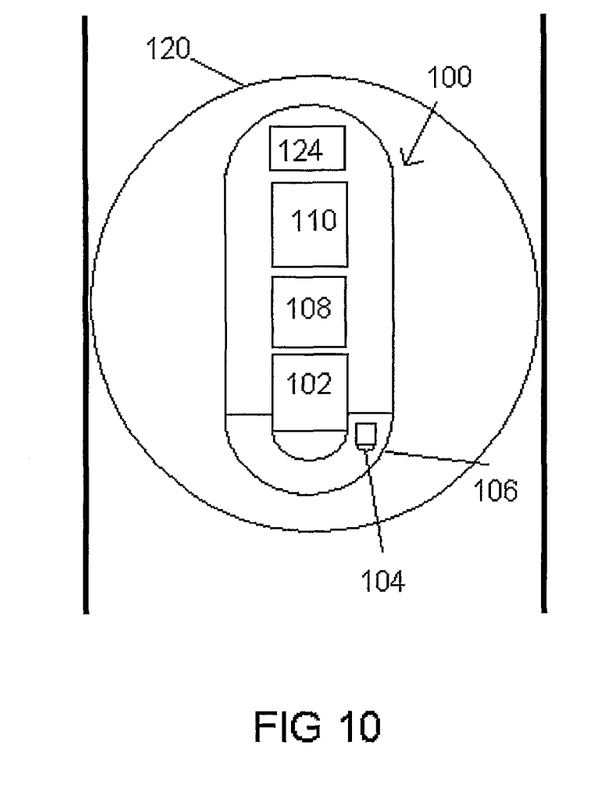
FIG. 10 shows an endoscopy capsule with a selectively inflatable bladder.

FIG. 10 shows an endoscopy capsule 100 with a selectively inflatable bladder or bladders 120. The bladder 120 can be selectively inflated and deflated by an inflation/deflation means 124 located within the endoscopy capsule 100. The inflation/deflation means 124 may operate using pressurized gas carried within the capsule, by a chemical reaction or by a miniature inflation/deflation pump within the capsule. The inflation/deflation means 124 may be controlled by signals, such as RF signals or magnetic signals, delivered from outside of the patient's body. The bladder 120 inflates approximately symmetrically around the endoscopy capsule 100 to contact the esophageal wall, for example to deliver a therapeutic treatment to the esophageal wall. Such therapeutic treatments could include cryogenic ablation, thermal ablation, RF ablation, ultrasonic ablation, laser ablation, phototherapy, radiation, brachytherapy, etc.

Figure 11:
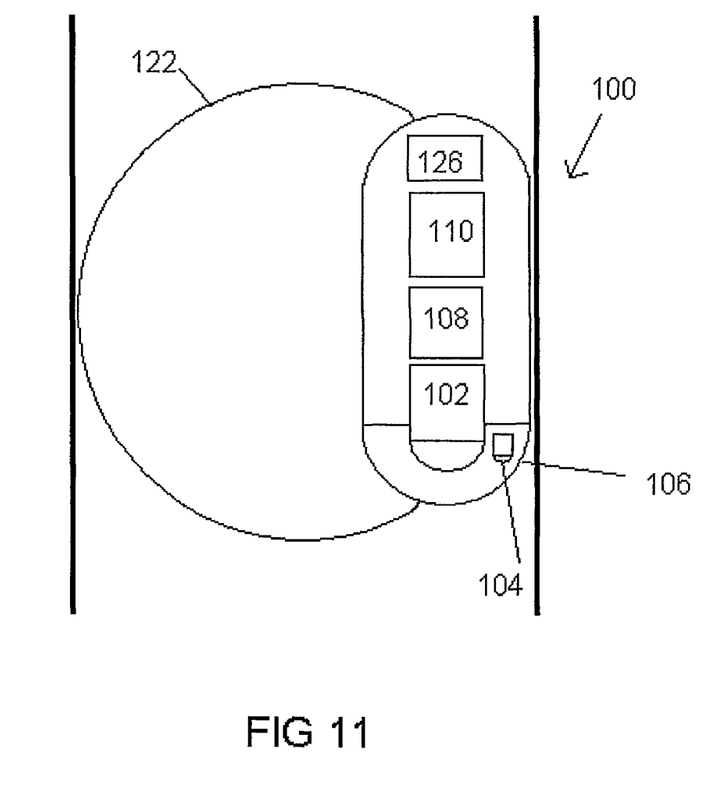
FIG. 11 shows an endoscopy capsule with an asymmetric selectively inflatable bladder.

FIG. 11 shows an endoscopy capsule 100 with an asymmetric selectively inflatable bladder 122. The bladder 122 can be selectively inflated and deflated by an inflation/deflation means 126 located within the endoscopy capsule 100. The inflation/deflation means 126 may operate using pressurized gas carried within the capsule, by a chemical reaction or by a miniature inflation/deflation pump within the capsule. The inflation/deflation means 126 may be controlled by signals, such as RF signals or magnetic signals, delivered from outside of the patient's body. When the bladder 122 inflates, the capsule 100 is pressed against the esophageal wall. The capsule 100 can deliver any of the therapeutic treatments to the esophageal wall discussed above and/or it can perform a diagnostic or therapeutic function that requires direct contact with the esophageal wall. For example, the capsule 100 can be configured to measure pH and/or temperature, inject medication, take biopsy samples or excise small polyps or other growths.

Figure 12:
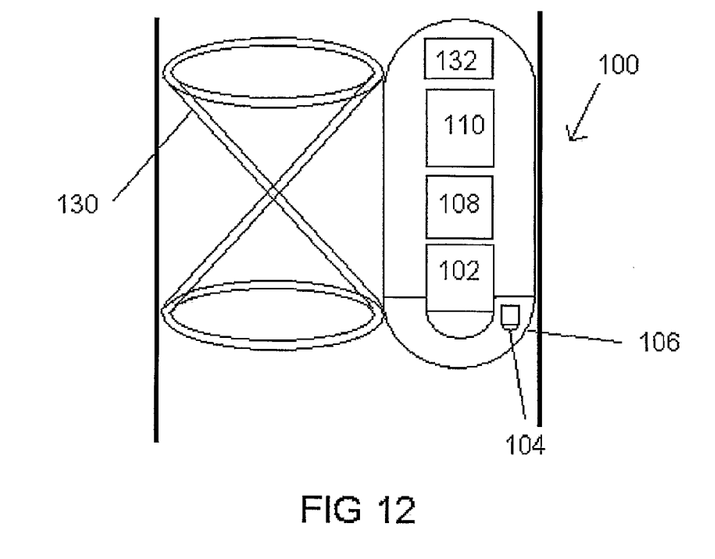
FIG. 12 shows an endoscopy capsule with a selectively expandable structure.

FIG. 12 shows an endoscopy capsule 100 with a selectively expandable structure 130. The selectively expandable structure 130 is the mechanical analog of the inflatable bladders of FIGS. 10 and 11 and can be configured to expand symmetrically or asymmetrically around the capsule 100. The selectively expandable structure 130 is configured with struts, hoops or other structures that can be activated with a shape memory material, with a microelectromechanical system (MEMS) or with pressurized chambers. An actuation means 132 for selectively expanding and contracting the structure 130 may be located within the endoscopy capsule 100. The actuation means 132 may be controlled by signals, such as RF signals or magnetic signals, delivered from outside of the patient's body. When the structure 130 expands, the structure 130 and/or capsule 100 is pressed against the esophageal wall. The capsule 100 can perform any of the diagnostic or therapeutic function discussed above.

Other possible features that may also be included in any of the embodiments of the endoscopy capsule 100 include:

The endoscopy capsule 100 may include means to deliver different wavelengths or spectra of light for different purposes. This can be accomplished by using different light sources 104 or by using a broad-spectrum light source 104 and one or more filters on the light source 104 and/or camera 102. For normal imaging, light in the visible range or white light is preferred. Other wavelengths can be used for different purposes instead of, or in addition to, normal imaging. For example, the endoscopy capsule 100 can be configured to do a spectroscopic examination, including chromoendoscopy, IR, UV, absorption, reflectance, transmission and/or fluorescence spectroscopy. Different CCD cameras 102 with different ranges of sensitivity may be used for different kinds of imaging or spectroscopy. Dyes may be applied to the esophageal wall to enhance imaging or spectroscopy. For example, the dye may be swallowed by the patient or it may be sprayed or injected by the endoscopy capsule 100.

Because it is controlled by the external magnets 202, 212, the endoscopy capsule 100 can make multiple passes up and down the esophagus, alternating between normal imaging and spectroscopy by switching between different light sources or filters.

Alternatively, the endoscopy capsule 100 may be configured to perform more than one kind of imaging simultaneously. For example, by alternating white light and light of a different wavelength and gating the imaging signals in timing with the light sources, a normal image and a spectroscopic image can be created at the same time. This can be accomplished by using a plurality of light sources 104 or by using one light source 104 and different filters. The images may be still images or video images or a combination of the two. Computer software can be used to separate and/or to combine the two images for enhanced diagnosis of different kinds of lesions. The images from the two imaging modalities may be viewed separately, displayed side-by-side and/or superimposed on one another in real time and/or in recorded images in order to facilitate diagnosis and treatment of the tissues being imaged.

Alternatively or in addition, the endoscopy capsule 100 may be configured to perform ultrasonic imaging. Ultrasonic imaging can be used to examine and/or measure the esophagus and surrounding tissues. Ultrasonic imaging can also be used for transesophageal echocardiography with much less discomfort for the patient than current methods.

The endoscopy capsule 100 may operate entirely on power stored in a battery. Alternatively, the endoscopy capsule 100 may include means to charge the battery from the outside, for example using inductive coupling, photovoltaic charging, etc. This may be important for more energy-demanding applications, such as endoscopic imaging or delivering therapeutic energy over an extended period. Alternatively, a thin wire or cable may extend out of the patient's mouth from the endoscopy capsule 100 for supplying energy and/or recharging the battery.

Any of the embodiments of the endoscopy capsule 100 may configured to perform a diagnostic or therapeutic function, including cryogenic ablation, thermal ablation, RF ablation, ultrasonic ablation, laser ablation, phototherapy, radiation, brachytherapy, measurement of pH and/or temperature, injection of medication, and biopsy or excision of small polyps or other growths. Depending on the clinical indications, therapy may be delivered to a specific lesion or to a general region of the esophagus. For example, the endoscopy capsule 100 may include means to activate a needle and push medication into a lesion or other area of the esophagus. The endoscopy capsule 100 may use an inflatable bladder or expandable structure to stabilize the capsule in position relative to an area to be treated as described above in connection with FIGS. 10-12. Alternatively or in addition, the endoscopy capsule 100 can be aimed and/or stabilized in position relative to an area to be treated using the first and/or second external magnets 202, 212 of the external capsule positioning system 200. The endoscopy capsule 100 can be controlled to perform the diagnostic and/or therapeutic functions by signals, such as RF signals or magnetic signals, delivered from outside of the patient's body.

Optionally, the endoscopy capsule 100 can be attached to a string or tether for retrieving the capsule from the patient's mouth.

The current invention includes apparatus and methods for spectroscopic imaging in capsule endoscopy. The capsule endoscopy will use any of the above spectroscopic techniques or any other spectroscopic technique to visualize dyplastic and abnormal tissue. Since the capsule endoscopy can use a tracking system to enable localization or identifying the location of the capsule in the gastrointestinal tract, the current invention also describes a combination of the spectroscopic visualization with regular light visualization. For example alternation of regular (visible) light with the spectroscopic light will enable the endoscopy capsule to collect two separate images of the GI tract.

The capsule may or may not be connected to the outside with a cord or cable(s). If not connected to the outside, the capsule may transmit the images to the outside or store the images inside the capsule. The images may be saved as a movie/video or as separate frames. One option is to separate the regular images/movie from the spectroscopic images/movie. One option is to project those images/movies side-by-side to correlate the anatomical findings (regular light) to the pathological findings (spectroscopy). Another option is to use external means (such as GPS technology, imagines studies or others) to locate the capsule relative to the body in order to locate where the pathology is. The capsule may include other features such as biopsy and therapy capabilities. The device will also be able to mark special locations in the GI tract by injecting dye, spraying colors or any other possible technique in order to mark where the pathology was found for a later therapy.

An example of a spectroscopic imaging technique that can be used with the present invention is protoporphyrin IX fluorescence, which has been shown to be useful for identifying areas of high-grade dysplasia in Barrett's esophagus.

Another imaging technology that can be used in the present invention is radionuclide imaging, known also as nuclear medicine scanning, which is a method for localizing diseases of internal organs by injecting small amounts of a radioactive substance (isotope) into the bloodstream. The isotope collects in certain organs or tissues and a special camera is used to produce an image of the organ and detect areas of disease. Several different isotopes are used in radionuclide imaging, including technetium 99m, indium 111, thallium 201, iodine 123, iodine 131, Gallium 67, Samarium 153, Strontium 89, and Xenon 133.

Examples of radionuclide imaging techniques that can be used include: tumor-specific monoclonal antibody radioimmunoscintigraphy, an imaging technique that uses radioisotope labeled antibodies for identifying cancer cells; radioisotope labeled polyclonal antibodies for identifying inflammatory disease (for example, nonspecific polyclonal immunoglobulin G (IgG) has been shown to localized as well as specific antibodies for identifying inflammatory bowel disease); radioisotope labeled white blood cells (leukocytes) for identifying inflammatory disease; radioisotope labeled cytokines for imaging chronic inflammation.

Another example of radionuclide imaging technique that can be used is a red blood cell scan that is used to diagnose bleeding. In this example, the capsule will be able to sense the radionuclide material that is added to the red blood cells and to identify areas of internal bleeding in a much more sensitive way than the techniques employed currently.

The endoscopy capsule will be configured to include a radiation detector sensitive to the emissions of the radioisotope used. The radiation detector can be configured to produce static or moving images of the area scanned. The images are recorded within the endoscopy capsule and/or transmitted to a receiver outside the body. Alternatively, if high spatial resolution is not needed, the radiation detector can be configured to simply detect and record and/or transmit the level of radiation as the endoscopy capsule passes through the digestive tract.

The endoscopy capsule can be configured to alternate between the visible light imaging and radionuclide imaging so that images from the two imaging modalities can be analyzed and compared to localize pathological conditions. Alternatively, if the two imaging modalities chosen do not interfere with one another, the visible light imaging and radionuclide imaging can be conducted continuously and simultaneously.

Figure 14:
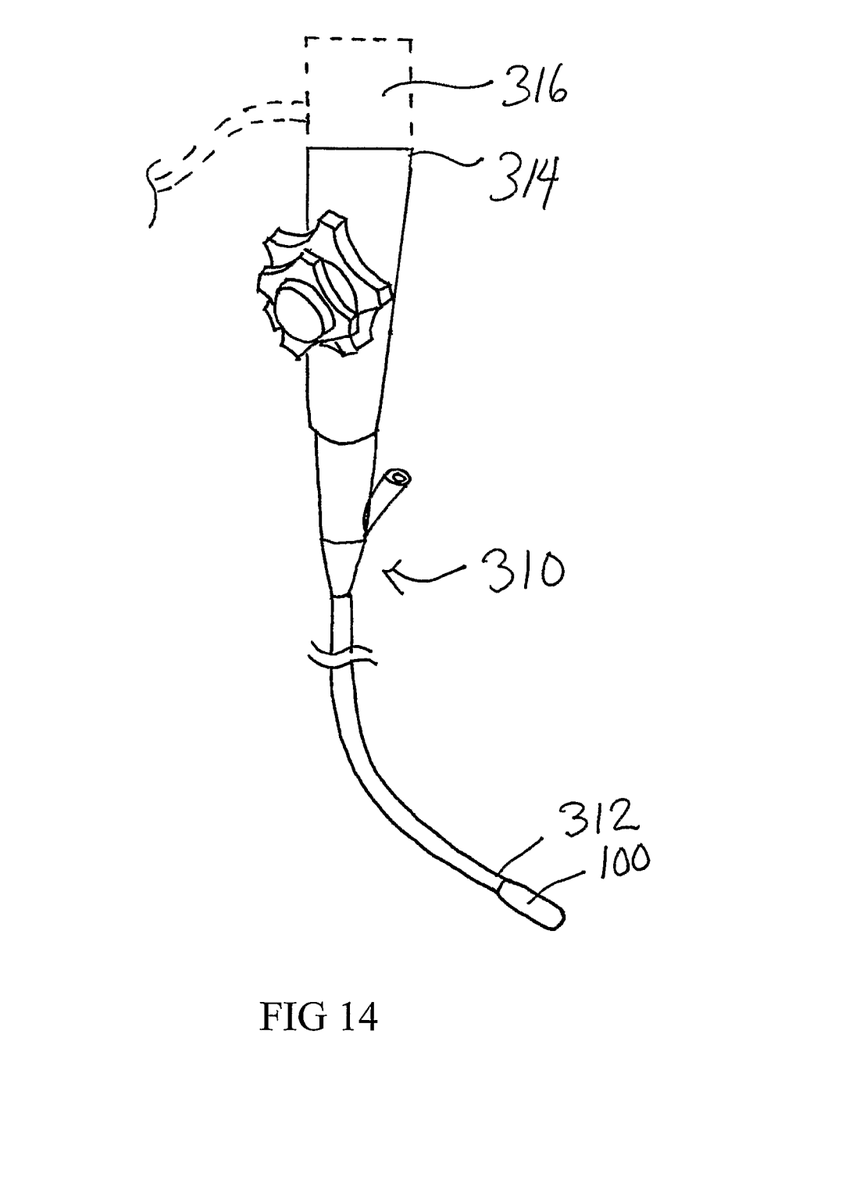
FIG. 14 illustrates a video endoscope with an imaging capsule mounted on the distal end for visible light and/or spectroscopic imaging.

The imaging modalities described herein can also be used in conjunction with a conventional optical endoscope or a video endoscope for visible light and/or spectroscopic imaging. For example, FIG. 14 illustrates a video endoscope 310 with an imaging capsule 100 mounted on the distal end. The imaging capsule 100 may be configured like any of the various embodiments of imaging capsules described herein. In particular, an imaging capsule 100 with two or more sources of illumination can be used for capturing both visible light and spectroscopic images of the internal anatomy. The imaging capsule 100 may be permanently or removably mounted to the distal end 312 of the endoscope 310. Images may be transmitted from the imaging capsule 100 by wireless transmission or through a cable in the endoscope 310. In various embodiments, the endoscope 310 may be a flexible endoscope, a robotically steerable endoscope or a rigid endoscope, depending upon the anatomy that is to be accessed and imaged using the device. If a conventional optical endoscope is used, an external imaging unit 316 containing the light source(s), imaging camera(s) and optional filter(s) can be mounted at the proximal end 314 of the endoscope 310 proximal to the optical imaging components of the endoscope. Another alternative is to place the light source(s) and optional filter(s) in an external imaging unit 316 and to place the imaging camera(s) at the distal end 312 of the endoscope 310, or vise versa.

The endoscope 310 can make multiple passes within the anatomy, alternating between normal visible light imaging and spectroscopy by switching between different light sources or filters in the imaging capsule 100 or the external imaging unit 316. Alternatively, visible light imaging and spectroscopic imaging may be performed simultaneously, for example, by alternating visible light and light of a different wavelength and gating the imaging signals in timing with the light sources. This can be accomplished by using a plurality of light sources 104 or by using one light source 104 and different filters, as described above. The images may be still images or video images or a combination of the two. Computer software can be used to separate and/or to combine the two images for enhanced diagnosis of different kinds of lesions. The images from the two imaging modalities may be viewed separately, displayed side-by-side and/or superimposed on one another in real time and/or in recorded images in order to facilitate diagnosis and treatment of the tissues being imaged.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. An endoscopic imaging apparatus, comprising:
    an ingestible endoscopy capsule including a magnetically attracted element; and
    an external capsule positioning system comprising a first track and a first magnet moveable on the first track, wherein said first track is configured to be fastened to a patient in a position approximately parallel with the patient's esophagus.

2. The endoscopic imaging apparatus of claim 1, wherein the magnetically attracted element of the endoscopy capsule comprises a permanent magnet.

3. The endoscopic imaging apparatus of claim 1, wherein the magnetically attracted element of the endoscopy capsule comprises an electromagnet.

4. The endoscopic imaging apparatus of claim 1, wherein the magnetically attracted element of the endoscopy capsule comprises a magnetically attracted ferritic material.

5. The endoscopic imaging apparatus of claim 1, wherein the magnet of the external capsule positioning system comprises a permanent magnet.

6. The endoscopic imaging apparatus of claim 1, wherein the magnet of the external capsule positioning system comprises an electromagnet.

7. The endoscopic imaging apparatus of claim 1, wherein the track is configured to be positioned on a ventral side of the patient.

8. The endoscopic imaging apparatus of claim 1, wherein the track is configured to be positioned on a dorsal side of the patient.

9. The endoscopic imaging apparatus of claim 1, wherein the first track is configured to be positioned on a ventral side of the patient, the capsule positioning system further comprising:
    a second track configured to be positioned on a dorsal side of the patient and a second magnet moveable on the second track,
    wherein the second track is configured to be fastened to the patient in a position approximately parallel with the patient's esophagus, and
    wherein the first and second magnets are configured to be moveable synchronously in order to move the endoscopy capsule along a desired path within the patient's anatomy.

10. The endoscopic imaging apparatus of claim 1, wherein the endoscopy capsule includes a visible light imaging component and a spectroscopic imaging component.

11. The endoscopic imaging apparatus of claim 1, wherein the endoscopy capsule includes an electronic memory for storing images within the capsule.

12. The endoscopic imaging apparatus of claim 1, wherein the endoscopy capsule includes a transmitter for transmitting images to an external receiver.

13. The endoscopic imaging apparatus of claim 1, wherein the track conforms to the curvature of the patient's torso.

14. The endoscopic imaging apparatus of claim 1, wherein the track is linear.

* * * * *